(12) United States Patent
Klein et al.

(10) Patent No.: US 11,541,008 B2
(45) Date of Patent: Jan. 3, 2023

(54) PHOSPHATIDYLCHOLINE LIPID LIPOSOMES AS BOUNDARY LUBRICANTS IN AQUEOUS MEDIA

(71) Applicants: YEDA RESEARCH AND DEVELOPMENT CO., LTD., Rehovot (IL); YISSUM RESEARCH DEVELOPMENT COMPANY OF THE HEBREW UNIVERSITY OF JERUSALEM, LTD., Jerusalem (IL)

(72) Inventors: Jacob Klein, Rehovot (IL); Ronit Goldberg, Rehovot (IL); Yechezkel Barenholtz, Jerusalem (IL); Avi Schroeder, Moshav Massuout Yitzhak (IL)

(73) Assignees: YEDA RESEARCH AND DEVELOPMENT CO., LTD., Rehovot (IL); YISSUM RESEARCH DEVELOPMENT COMPANY OF THE HEBREW UNIVERSITY OF JERUSALEM, LTD., Jerusalem (IL)

(*) Notice: Subject to any disclaimer, the term of this patent is extended or adjusted under 35 U.S.C. 154(b) by 0 days.

(21) Appl. No.: 16/809,816

(22) Filed: Mar. 5, 2020

(65) Prior Publication Data
US 2020/0338001 A1     Oct. 29, 2020

Related U.S. Application Data

(62) Division of application No. 13/704,866, filed as application No. PCT/IL2011/000477 on Jun. 16, 2011, now abandoned.
(Continued)

(51) Int. Cl.
*A61K 9/127*     (2006.01)
*A61L 27/50*     (2006.01)

(52) U.S. Cl.
CPC .............. *A61K 9/127* (2013.01); *A61L 27/50* (2013.01); *A61L 2400/10* (2013.01); *A61L 2430/24* (2013.01)

(58) Field of Classification Search
CPC .......... A61K 9/127; A61K 8/21; A61K 8/602; A61K 8/731; A61L 27/50; A61L 2430/24; A61L 2400/10; A61Q 11/00
See application file for complete search history.

(56) References Cited

U.S. PATENT DOCUMENTS 5,135,669 A * 8/1992 Brois ............... C10L 10/08
                                                       508/428
5,304,380 A   4/1994 Miyajima
(Continued)

FOREIGN PATENT DOCUMENTS

WO    WO 03/000190     1/2003
WO    WO 2008/038292   4/2008

OTHER PUBLICATIONS

Verberne, G., et al in Wear, vol. 268, pp. 1037-1042, 2010.*
(Continued)

*Primary Examiner* — Gollamudi S Kishore
(74) *Attorney, Agent, or Firm* — Nixon & Vanderhye, P.C.

(57) ABSTRACT

The invention provides a method for lubricating one or more surfaces, comprising applying gel-phase liposomes onto said one or more surfaces, wherein the temperature of said surface(s) at the time of lubrication is below the phase transition temperature $T_m$ of said liposomes. The method can be used for lubricating non-biological surfaces, and also for lubricating the surfaces of a biological tissue in a mammalian subject, e.g., for treating joint dysfunction.

9 Claims, 10 Drawing Sheets

Related U.S. Application Data

(60) Provisional application No. 61/355,573, filed on Jun. 17, 2010.

(56) References Cited

U.S. PATENT DOCUMENTS

| | | | | |
|---|---|---|---|---|
| 5,688,496 | A * | 11/1997 | Fost | A61K 8/896 424/70.122 |
| 6,800,298 | B1 | 10/2004 | Burdick et al. | |
| 7,749,485 | B2 | 7/2010 | Tournier | |
| 8,263,118 | B2 * | 9/2012 | Callegaro | A61K 9/127 424/450 |
| 8,895,054 | B2 * | 11/2014 | Barenholz | A61L 27/50 424/450 |
| 2003/0139344 | A1 | 7/2003 | Hung | |
| 2004/0067196 | A1 | 4/2004 | Brunke | |
| 2004/0191306 | A1 | 9/2004 | Zhang | |
| 2005/0069576 | A1 | 3/2005 | Mills | |
| 2005/0123593 | A1 | 6/2005 | Thompson | |
| 2005/0164981 | A1 | 7/2005 | Burdick | |
| 2007/0026061 | A1 * | 2/2007 | Ali | A61K 9/127 424/450 |
| 2009/0155375 | A1 * | 6/2009 | Tonge | A61K 8/553 514/1.1 |
| 2011/0171288 | A1 | 7/2011 | Mohammadi | |
| 2012/0183596 | A1 | 7/2012 | Boulikas | |
| 2013/0323165 | A1 | 12/2013 | Campbell | |

OTHER PUBLICATIONS

Sivan, S in Langmuir, vol. 26, #2, pp. 1107-1116, 2010.*
Office Action dated Jul. 1, 2015 From the Israel Patent Office Re. Application No. 223518.
International Preliminary Report on Patentability dated Jan. 3, 2013 From the International Bureau of WIPO Re. Application No. PCT/IL2011/000477.
Communication Pursuant to Article 94(3) EPC dated Oct. 16, 2015 From the European Patent Office Re. Application No. 11743371.4.
Communication Pursuant to Rules 161(1) and 162 EPC dated Feb. 22, 2013 From the European Patent Office Re. Application No. 11743371.4.
International Search Report for PCT/IL2011/000477 dated Oct. 13, 2011.
Written Opinion of the International Searchina Authority dated Oct. 13, 2011.
Bard, D.R., et al. Bard et al (Clin. and Experimental Rheumatology, vol. 1, pp. 113-117, 1983).
Bard et al (Clin. and Experimental Rheumatology, vol. 3, pp. 237-242, 1985).
Tadmor et al., "Normal and Shear Forces between Mica and Model Membrane Surfaces with Adsorbed Haluronan" *Macromolecules*, vol. 36: 9519-9526 2003.
Zappone et al., "Adsorption, Lubrication, and Wear of Lubricin on Model Surfaces: Polymer Brush-Like Behavior of a Glycoprotein" *Biophysical Journal*, vol. 92: 1693-1708 Mar. 2007.
Sivan et al., Liposomes Act as Effective Biolubricants for Friction Reduction in Human Synovial Joints, Langmuir, 26(2), 1107-1116 (2010).
Verberne et al. "Liposomes as Potential Biolubricant Additives for Wear Reduction in Human Synovial Joints", Wear, XP026924037, 268(7-8): 1037-1042, Available Online Dec. 28, 2009.
Chen et al., "Lubrication at Physiological Pressures by Polyzwitterionic Broshes," Science, vol. 323, Mar. 27, 2009, pp. 1698-1701.
Vecchio et al., "Rheumatology," Letters to the Editor, 1999, pp. 1020-1021.
Afoke, et al., "Contact Pressures in the Human Hip Joint", The Journal of Bone and Joint Surgery from the Polytechnic of Central London, Faculty of Engineering and Science, School of Mechanical and Computer Aided Engineering, 115 New Cavendish Street, London WIM 8JS, England, ., pp. 536-541 (6 pages), 1987.

* cited by examiner

PHOSPHATIDYLCHOLINE LIPID LIPOSOMES AS BOUNDARY LUBRICANTS IN AQUEOUS MEDIA

This application is the divisional of U.S. application Ser. No. 13/704,866 filed Feb. 8, 2013, wherein 13/704,866 is the national stage entry of. PCT/IL2011/000447 filed Jun. 16, 2011 which is designated to the U.S. and claims priority from provisional application 61/355,573 filed Jun. 17, 2010, the entire contents of each of which are hereby incorporated by reference.

BACKGROUND

Liposomes are vesicles whose membranes in most cases are based on phospholipid bilayers. They are generally biocompatible and, when modified with other molecules, are widely used in clinical applications, primarily as drug delivery vehicles, as well as in gene therapy and for diagnostic imaging.

WO 08/038292, by some of the present inventors, disclosed, inter alia, multilamellar vesicles (MLVs) of several phospholipids above their liquid-crystalline-phase to gel-phase transition temperature Tm as possible boundary lubricants in the articular cartilage environment.

Presently, there is a serious lack of good solutions to the problem of boundary lubrication in aqueous media. Boundary lubrication in aqueous media is often problematic as water on its own is not a good lubricant, while common surfaces or surface coatings in water frequently exhibit quite high friction (with friction coefficients $\mu > 0.01$-$0.05$), especially at high pressures.

The problem is even more evident when extremely low friction is required, particularly at high pressures (up to 100 atmospheres or more) and at low sliding velocities. For example, Values of ca. $2 \times 10^{-3}$ or lower have been measured between some physically-attached boundary lubricants, but these were at mean contact pressures of only up to 0.3 MPa (3 atmospheres) or less. In Chen, M., Briscoe, W. H., Armes, S. P., and Klein, J [Lubrication at Physiological Pressures by Polyzwitterionic Brushes, *Science* 323, 1698 (2009)] it is reported that boundary lubricants which were covalently grown on surfaces demonstrate low friction coefficients, around $10^{-3}$, up to 75 atmospheres pressure.

Vecchio, P.; Thomas, R.; Hills [B. A. Rheumatology 1999, 38(10), 1020-1021] describe the injection of dipalmitoylphosphatidylcholine (DPPC) solutions in propylene glycol into joints.

U.S. Pat. No. 6,800,298 describes a lubricant composition comprising dextran-based hydrogel with lipids.

There is a need for an alternative physically-attached boundary lubricant in aqueous media, which would have a low friction coefficient even at contact pressures substantially higher than 0.3 MPa.

SUMMARY OF THE INVENTION

It has now been surprisingly found that it is possible to use gel-phase liposomes as lubricants. Liposomes are known to transform from their gel (solid) phase to liquid crystalline phase at a characteristic temperature designated $T_m$, defined as the temperature at which the maximal change in the excess heat capacity (kcal/mol/deg) occurs. The lubrication properties of gel phase liposomes, namely, liposomes applied onto surfaces at a temperature which is lower than their $T_m$, were tested and were found to be particularly good. It has been found that gel-phase liposomes are especially useful for lubricating surfaces that are subject to high pressure, up to 120 atmospheres (around 120 MPa) or more. Notably, when the pressure exerted over the surface is above 30 atmospheres (3 MPa), then the lubrication provided by the gel-phase liposomes, is better than that of liquid-phase liposomes. Thus, the gel-phase liposomes may be used according to the invention for the treatment of joint dysfunction, wherein the pressure within the joint reaches values in the range of 30 to 120 atmospheres (3-12 MPa). Characteristic pressures in joints are reported in the following references:

1. Afoke, N. Y. P., Byers, P. D., and Hutton, W. C., Contact pressures in the human hip joint. *J. Bone Joint Surgery* 69B, 536 (1987).
2. Hodge, W. A., Fuan, R. S., Carlson, K. L., Burgess, R. G., Harris, W. H., and Mann, R. W., Contact pressures in the human hip joint measured in vivo. *Proc. Natl. Acad. Sci. USA* 83, 2879 (1986).

As demonstrated in the experimental section below, gel-phase liposomes of different compositions and size characteristics can provide efficient lubrication in aqueous environments on solid surfaces on which they spontaneously adsorb to form surface coatings. The lubrication (yielding, in most cases, values $\mu <$ ca. $1 \times 10^{-3}$) occurs under pressures of up to 120 atmospheres or more, and down to very low sliding velocities, with little apparent wear of the liposome surface coatings.

Thus, in a first aspect, the invention provides a method for lubricating one or more non-biological surfaces (in particular negatively charged solid surfaces), comprising applying gel-phase liposomes onto said one or more surfaces, wherein the temperature of said surface(s) at the time of lubrication is below the phase transition temperature $T_m$ of said liposomes.

The invention also provides a method for lubricating one or more surfaces of a biological tissue in a mammalian subject (for example, a cartilage surface within a joint capsule), comprising applying gel-phase liposomes onto said one or more surfaces, wherein the temperature of said surface(s) at the time of lubrication is below the phase transition temperature $T_m$ of said liposomes. The use of gel-phase liposomes for lubricating surfaces having a surface temperature which is below the phase transition temperature $T_m$ of said liposomes, constitutes another aspect of the invention. The invention also encompasses a therapeutic composition for lubricating the surface of a biological tissue in a mammalian subject, wherein said composition comprises gel-phase liposomes and an aqueous carrier.

More specifically, the invention provides the use of gel-phase liposomes in the preparation of a therapeutic composition for the treatment of joint dysfunction in a mammalian subject by means of the lubrication of cartilage surface(s) within the joint capsule, wherein the temperature of said surfaces at the time of lubrication is below the phase transition temperature $T_m$ of said liposomes. The invention also provides gel-phase liposomes for the treatment of joint dysfunction in a mammalian subject by means of the lubrication of surface(s) within the joint capsule, wherein the temperature of said surfaces at the time of lubrication is below the phase transition temperature $T_m$ of said liposomes. The maximal pressure within the joint is in the range of 30 to 120 atmospheres (3-12 MPa). The carrier used for administering the liposomes to the mammalian subject is preferably an aqueous carrier (e.g., an aqueous-based buffer solution) free of organic co-solvents or extraneous organic compounds (other than of course the liposomes).

Gel-phase Liposomes to be used according to the invention are based on phosphocholine-containing lipids and mixtures thereof. However, it is possible to combine lipids having polar head groups other than phosphocholine in the gel-phase liposomes. Liposomes operable in the invention have external (exposed at the outer liposome surface) polar head groups which are composed of at least 95 mole % phosphocholine groups, and of up to 5 mole % external non-phosphocholine head group having an unperturbed-end-to-end radius in aqueous medium equal to or smaller than about 1 nm, or cross-section parameter which is less than 0.8 nm$^2$, (provided, of course that said liposomes are in their gel-phase and have a T$_m$ which is higher than the intended working temperature).

In contrast, liposomes in which the up to 5 mole % external non-phosphocholine head group units have an unperturbed-end-to-end radius (in the aqueous medium) which is larger than about 1 nm, are not suitable for use as lubricant compositions since the systems formed by incubating the solid surfaces therein have a high friction coefficient. For example, liposomes in which the 5% of external non-phosphocholine head groups were the PEG groups of DSPE-PEG2000, having an unperturbed-end-to-end radius (in aqueous medium) of about 4 nm, demonstrated poor lubrication properties, having friction coefficients of 0.05 to 0.1 (Example C7, see below).

As noted above, the presence of head groups other than phosphocholine units in the gel-phase liposomes is permitted, provided that the unperturbed-end-to-end radius of said non-phosphocholine groups is less than 1 nm, or their cross section is less than 0.8 nm$^2$.

The term "unperturbed-end-to-end radius" means the steric size of said head group when it is not subject to external constraints, and is used herein in order to estimate the radius of non-phosphocholine head groups which are polymer chains (such as PEG chain in the case of DSPE-PEG2000 lipid) and also for non-phosphocholine head groups which are molecular/cationic entities (such as the TAP group in the 1,2-dimyristoyl-3-trimethylammonium-propane (DMATP)).

By way of the example, the size of the charged headgroup on the DMTAP is approximately 0.3-0.5 nm and its radius would be about half of that, say 0.2 nm. Thus, lipids which contain the TAP head group (and two hydrocarbon saturated chains) can be combined with phosphocholine-containing lipids to form liposomes which are suitable for use in the invention.

An alternative way for estimating the size of the polar head group of the lipid is by means of its cross section parameter, as described by Lewis, R. N. A. H., S. Tristram-Nagle, J. F. Nagle, and R. N. McElhaney[The thermodynamic phase behavior of cationic lipids: calorimetric, infrared spectroscopic and X-ray diffraction studies of lipid bilayer membranes composed of 1,2-di-O-myristoyl-3-N,N, N-trimethylaminopropane (DM-TAP). Biochim. Biophys. Acta. 1510:70-82, 2001].

In the case of non-phosphocholine head groups which are polymer chains with N backbone units, characteristic ratio C$_\infty$ and mean backbone unit size x, the unperturbed-end-to-end radius R$_0$ is given by:

$$R_0 = (NC_\infty)^{1/2} x$$

For the particular case of polyethylene glycol (PEG) of molecular weight 2000, say, the number of backbone units is N=2000/(44/3), C$_\infty$=4.9±0.1, and x≈0.15 nm, so that the unperturbed-end-to-end radius in this case is R$_0$=ca. 3.9 nm.

Preferably, the gel-phase liposomes used according to the invention comprise one or more phosphatidylcholine lipids, with the T$_m$ values of the liposomes being not less than 40° C., preferably not less than 45° C. Mixtures of different phosphatidylcholine lipids can be used to form the liposomes, with the molar ratio between the components of the mixture being adjusted to produce liposomes having the desired T$_m$ value [see Scott et al., Biophysical Journal (28), p. 117-132 (1979)]. According to one embodiment of the invention, T$_m$ is not less than 50° C., e.g., from 50 to 60° C. According to one embodiment, the hydrocarbon tails of the phosphatidylcholine lipids are saturated and contain not less than 17 carbon atoms. In particular, it has now been found that liposomes comprising hydrogenated soy phosphatidylcholine (HSPC), 1,2-distearoyl-sn-glycero-3-phosphocholine (DSPC) and dipalmitoylphosphatidylcholine (DPPC) and mixtures thereof may act as efficient lubricants in aqueous media even at physiologically high pressures of up to 120 atmospheres (85% of the HSPC are DSPC and 15% are the sum of 1 stearoyl 2-palmitoyl PC plus 1-palmitoyl 2-steroyl PC). The T$_m$ values for HSPC, DSPC and DPPC are 52.5° C., 55° C. and 41.4° C., respectively. T$_m$ values of various PC-based lipids may be found in "Thermotropic Phase Transitions of Pure Lipids in Model Membranes and Their Modifications by Membrane Proteins", John R. Silvius, Lipid-Protein Interactions, John Wiley & Sons, Inc., New York, 1982, and also in the Lipid Thermotropic Phase Transition Data Base-LIPIDAT.

According to another preferred embodiment of the invention, the liposomes to be used are in the form of small unilamellar vesicles (SUV). For example, it has been shown that small unilamellar vesicles (SUVs) of hydrogenated soy phosphatidylcholine (HSPC) lipids self-assembled in close-packed layers on solid surfaces, thereby reducing the coefficient μ of sliding friction between these surfaces down to values μ≈10$^{-4}$-2×10$^{-5}$, at pressures of up to ca. 12 MPa (ca. 120 atmospheres) and possibly higher. Such low values of the friction have so far been attained in other physically-attached boundary lubricants only at mean contact pressures of up to 0.3 MPa or less, these being lower by up to 40-fold or more than the pressures reached with the presently disclosed liposome composition (12 MPa). According to another preferred embodiment, the SUV liposomes have a mean diameter which is smaller than 100 nm. Good to excellent lubrication between solid surfaces coated by SUVs of 1,2-distearoyl-sn-glycero-3-phosphocholine (DSPC) and by SUVs of 1,2-dipalmitoyl-sn-glycero-3-phosphocholine (DPPC), has also been achieved at comparably high pressures as seen in Table 1 and described below.

Thus, according to a preferred embodiment, at least 95% of the external polar head groups of the gel-phase liposomes used in the method of the invention are phosphoryl choline head group, the liposomes being in the SUV form and having a mean diameter which is smaller than 100 nm. Preferably, these gel-phase SUV PC-based liposomes have a mean diameter ranging from about 60 nm to about 80 nm, more preferably ranging from about 65 nm to about 75 nm.

Furthermore, it has been shown that multilamellar vesicles (MLVs) of hydrogenated soy phosphatidylcholine (HSPC) lipids self-assembled on solid surfaces, and effectively reduced the coefficient μ of sliding friction between these surfaces down to values in the range of μ=7×10$^{-3}$ to 5×10$^{-4}$, for both first and second approaches as pressures are up to 3 Mpa (~30 atm).

Thus, according to yet another preferred embodiment of the invention, the liposomes in the compositions described herein, are in the form of multilamellar vesicles (MLVs). Preferably, these liposomes have a mean diameter larger than 200 nm, yet more preferably larger than 500 nm, and most preferably of about 1 micron and larger.

Preferred liposomes to be used according to the invention, for example for lubricating non-biological surfaces, consist of HSPC, DSPC or DPPC lipids. These PC-based liposomes exhibit good to excellent lubrication results under various conditions, as can be seen in Examples S1, S2, S3, S6, S10 and S11.

Another class of preferred liposomes to be used according to the invention, for example for lubricating non-biological surfaces, is based on a mixture comprising a first lipid, which is phosphocholine-containing lipid (e.g., HSPC, DSPC or DPPC, or their mixtures) and a second lipid, which contains TAP hydrophilic head group, wherein the mole ratio between said first and second lipids is from 95:5 to 99.9:0.1. The second lipid, namely, the TAP-containing lipid has two hydrocarbon chains which independently contain 14, 16 or 18 carbon atoms. Preferably, the TAP-containing liposome is selected from the group consisting of 1,2-ditetradecanoyl-3-trimethylammonium-propane (DMTAP), 1,2-dipalmitoyl-3-dimethylammonium-propane and 1,2-disteraroyl-3-dimethylammonium-propane, which are also described as 14:0 TAP, 16:0 TAP and 18:0 TAP, respectively, indicating that the length of both chains of the lipid is the same (being 14, 16 and 18, respectively). The "mixed" liposome exhibits very good lubrication results under various conditions, as can be seen in Examples S4 and S5. The mixed liposomes having the composition set for the above are believed to be novel and form a further aspect of the present invention.

It should be noted that the good lubrication results were obtained for different aqueous mediums, for example in pure water, as well as in physiological salt solution.

Furthermore, the good lubrication was obtained also when the surface of the liposomes was positively charged (for example, when some of the zwiterionic HSPC molecules were replaced by charged DMTAP cationic lipids).

It has been found that liposomes having positively charged surface showed improved lubrication with the negatively-charged solid surfaces in water at high salt concentrations (for example, not less than 0.05M of a 1:1 salt, e.g., not less than 0.15M), as compared to liposomes having positively charged surface used in water containing no added salt.

Thus, according to preferred embodiments of the invention, the gel-phase liposomes to be used have positively charged surfaces.

As shown hereinbelow, the liposomes used according to the present invention adsorb spontaneously onto negatively charged solid surfaces in water, to form close-packed boundary layers that provided uniquely efficient lubrication, resulting in friction coefficients down to $2\times10^{-5}$ at pressures of more than 100 atmospheres (above 10 MPa). This extremely low friction at such high pressures makes these liposomes extremely suitable for providing efficient lubrication in aqueous media. It should be understood, however, that the surfaces to be treated by the liposomes in accordance with the invention may be overall neutral, but having discrete positive and negative regions, such that the liposomes attach to the negatively-charged regions, or even to overall-positively charged surfaces if there are also negatively charged patches on them onto which the liposomes may attach. Positively-charged surfaces can also be treated with gel-phase phosphatidylcholine liposomes with up to 5 mole % of negatively-charged lipids such as phosphatidic acid (PA), phopsphatidyl glycerol (PG), phopsphatidyl inositil (PI) and phosphatidylserine (PS).

Thus, according to another aspect of the invention, there is provided a lubricant system comprising a plurality of liposomes being in their gel-phase and further being spontaneously adsorbed on at least one of two negatively charged solid surfaces, in an aqueous medium. The characteristics of the liposomes are as set forth above.

Suitable negatively charged solid surfaces include, but are not limited to, glass, mica and cartilage.

For example, the gel-phase liposomes to be used according to the invention proved as efficient lubricants when coated on one or two mica surfaces, having friction coefficients lower than $1\times10^{-2}$ and even lower than $5\times10^{-3}$ and $15\times10^{-4}$.

Thus, according to preferred embodiments of the invention, the lubricant system described herein has a coefficient of sliding friction between the above-described surfaces which is less than about $1\times10^{-2}$ under a pressure of at least 1 Mpa, in the aqueous medium.

The improved friction results were obtained even at high pressures (much higher than 0.3 MPa as known in the art for physically-attached boundary lubricants), namely pressures which were at least 1 Mpa, 3 Mpa, 6 Mpa and 10 Mpa, even reaching 12 MPA. It is believed that the improved friction shall be exhibited even at higher pressures.

Furthermore, the good lubrication under pressure is now maintained repeatedly, for a large number of additional back-and-forth sliding cycles. This phenomenon is important since under physiological solutions, normal application of lubricants may involve very large numbers of repetitive cycles. According to the present invention, not only does the lubricant remain attached or adsorbed to the surface upon application of pressure, but it may remain so even after additional similar pressure cycles.

These findings demonstrate that the liposomes described herein may reduce friction between surfaces onto which they spontaneously adsorb, up to the maximal pressures pertaining in mammalian joints, to levels that are even lower than between healthy sliding articular cartilage. Such low friction between surfaces in aqueous media at these high pressures has not hitherto been attained by any physically-attached boundary lubricant system.

Thus, according to another aspect of the invention, there is further provided a method of decreasing the friction coefficient between two negatively charged solid surfaces in aqueous medium to below about $1\times10^{-2}$ under a pressure of at least 1 MPa, the method comprising incubating one or both of the surfaces in a lubricant comprising a plurality of liposomes being in their gel-phase and dispersed in an aqueous medium. The characteristics of the liposomes are as set forth above.

According to preferred embodiments of the invention, the method can decrease the coefficient of sliding friction to below about $5\times10^{-3}$, and even to below about $5\times10^{-4}$.

Most advantageously, this can be achieved and maintained even at high pressures, preferably of at least 3 Mpa, and even at a pressure which is at least 10 MPa.

In order to effectively reduce the friction coefficient as described herein, the liposome used is as described in detail hereinabove. Furthermore, the incubation is preferably conducted for at least 0.5 hours, for example from 1.5 to 2 hours. However, it should be noted that the surfaces can be left under incubation for prolonged periods of time (for example several days) without adversely effecting the adsorption of the liposomes to the surfaces.

The incubation as described in the examples was conducted at about room temperature, but this can vary according to the desired application.

As already noted above, the gel-phase liposomes can also be used for the treatment of joint dysfunction in a mammalian subject by means of the lubrication of surface(s) within the joint capsule, wherein the temperature of said surfaces at the time of lubrication is below the phase transition temperature $T_m$ of said liposomes. The gel-phase liposomes may be used to treat, alleviate, retard, prevent, manage or cure any articular disorder or symptoms arising there from which is associated with joint dysfunction. For the purposes of this disclosure the term "articular disorder" shall be held to mean any affliction (congenital, autoimmune or otherwise), injury or disease of the articular region which causes degeneration, pain, reduction in mobility, inflammation or physiological disruption and dysfunction of joints. The disorder may be associated with reduced joint secretion and lubrication as well as from complications of knee and hip replacement.

The joint in accordance with the invention may be any one of the knee, hip, ankle, shoulder, elbow, tarsal, carpal, interphalangeal and intervertebral.

Specific articular disorders include, but are not limited to, deficiencies of joint secretion and/or lubrication arising from arthritis, including conditions of joint erosion in rheumatoid arthritis, osteoarthritis, osteoarthritis in rheumatoid arthritis patients, traumatic joint injury (including sports injury), locked joint (such as in temporomandibular joint (TMJ)), status post arthrocentesis, arthroscopic surgery, open joint surgery, joint (e.g. knee or hip) replacement in mammals, preferably humans. A specific disorder to be treated or prevented by the method of the invention is osteoarthritis.

The method of the present invention could be used as a prophylactic measure to prevent future damage or degeneration. For example, the gel-phase liposomes could be administered intra-articularly to athletes intermittently throughout their career to minimize the risk of stress related injury or cartilage degeneration.

The method of the present invention may be used exclusive of, or as an adjunct to, anti-inflammatory agents, analgesic agents, muscle relaxants, anti depressants, or agents that promote joint lubrication commonly used to treat disorders associated with joint stiffness, such as arthritis. A combined therapeutic approach is beneficial in reducing side effects associated with agents, such as non-steroidal, anti-inflammatory drugs (NSAIDs), commonly used to prevent, manage, or treat disorders such as osteoarthritis associated with reduced joint lubrication. In addition to enhancing safety, a combined therapeutic approach may also be advantageous in increasing efficacy of treatment.

The administration of the liposomes into an articular cavity of a patient may be by a method chosen from the group consisting of intra-articular injection, arthroscopic administration or surgical administration.

In accordance with one embodiment, the liposomes are administered to the mammalian subject using a physiologically acceptable carrier, such as histidine buffer (HB).

The composition according to the invention is preferably in a form suitable for administration by a route selected from intra-articular injection, arthroscopic administration or surgical administration.

The amount of liposomes to be administered will vary depending on the liposome's composition, the disease, its severity and treatment regimen, as well as on the age, weight, etc., of the mammal to be treated. The amount for purposes herein is determined by such considerations as may be known in the art.

The amount must be effective to achieve an improvement in the lubrication of the treated joint, namely, to reduce friction between the cartilages forming the joint, the improvement may be exhibited by clinical tests as well as by an improvement in the well-being of the subject undergoing said treatment (e.g. reduced pain in the afflicted joint, improvement in mobility). The effective amount is typically determined in appropriately designed clinical trials (dose range studies) and the person versed in the art will know how to properly conduct such trials in order to determine the effective amount. For example, the concentration of the liposomes in the aqueous carrier may be between 30 and 150 mM.

DETAILED DESCRIPTION

Table 1 below summarizes the lubricant compositions prepared according to preferred embodiments of the invention, and adsorbed on one or two molecularly smooth mica surfaces, as well as the lubrication properties of the obtained systems:

a) System S1, composed of two mica surfaces coated by small unilamellar vesicles (SUVs) of hydrogenated soy phosphatidylcholine (HSPC) liposomes in pure water. This system showed excellent levels of lubrication, having a friction coefficient $\mu \approx 10^{-4}$-$2 \times 10^{-5}$ up to pressures of 12 MPa (120 atmospheres) or more;

b) System S2, composed of a bare mica and a mica coated with SUV HSPC liposomes in pure water. This system showed, for regular high surface coverage, very good levels of lubrication, $\mu \approx 10^{-4}$, up to pressures of ca. 6 Mpa.

c) System S3, composed of SUV HSPC liposomes in physiological salt concentration of 150 mM $NaNO_3$. This system showed good level of lubrication between two coated mica surfaces, $\mu \approx 2*10^{-4}$-$10^{-2}$ at pressures up to 6 MPa.

d) System S4, composed of positively charged SUV HSPC/DMTAP liposomes in water. This system showed very good lubrication between two coated mica surfaces, $\mu \approx 10^{-4}$, up to pressures of ~3 MPa; for one coated surface vs. mica, $\mu \approx 3.5*10^{-2}$, at pressures up to ~1.3 MPa;

e) System S5, composed of positively charged SUV HSPC/DMTAP liposomes in physiological salt concentration of 150 mM $NaNO_3$; This system showed very good levels of lubrication between two coated surfaces, with $\mu \approx 2*10^{-4}$-$3 \times 10^{-3}$ up to pressures of ~6 Mpa, f) System S6, composed of multilamellar vesicles (MLVs) of HSPC liposomes. This system showed good lubrication between one coated surface and a bare mica surface, $\mu \approx 5*10^{-4}$-$7*10^{-3}$ at pressures up to 30 Mpa, g) System S10, composed of two surfaces coated by SUVs of 1,2-distearoyl-sn-glycero-3-phosphocholine (DSPC) liposome in pure water. This system showed excellent levels of lubrication, having a friction coefficient $\mu \approx 1.5 \times 10^{-4}$-$7 \times 10^{-5}$ up to pressures of 11 Mpa (110 atmospheres) or more; and h) System S11 composed of two surfaces coated by SUVs of 1,2-dipalmitoyl-sn-glycero-3-phosphocholine (DPPC) liposome in pure water. This system showed diverse values of effective friction coefficient $\mu$ and maximal applied pressure (before friction coefficient is increased). At the optimal contact points, the system showed excellent levels of lubrication, having a friction coefficient $\mu \approx 2 \times 10^{-4}$ up to pressures of 12 MPa (120 atmospheres) or more. However, due to the range of results over different contact positions and a tendency of the friction coefficient to increase at second and more entries to contact point, the overall lubrication efficiency of this system is estimated as good, level 3 (Table 1) (rather than excellent, level 5).

In addition, Table 2 below shows some comparative lubricant compositions adsorbed on one or two molecularly smooth mica surfaces, and the lubrication properties of the obtained systems:

a) System C7, composed of SUV PEGylated-HSPC liposomes in water, is a comparative example. This system showed poor lubrication levels, with $\mu \approx 0.05$-$0.1$ at pressures up to ca. 2.5 Mpa; and System C8, composed of SUV of 1-palmitoyl-2-oleoyl-sn-glycero-3-phosphocholine (POPC) liposomes in water, is another comparative example; This system showed poor lubrication levels, for $2^{nd}$ approach $\mu \approx 0.1$ up to 3 MPa pressures.

In both tables, Liposomes lubrication efficiency was scored by the inventors according to the shear reduction measured in the experimental system—the surface force balance. Value of 5 was given to the best lubrication capability as 1 to the worst.

TABLE 1

| Short name | Chemical composition | SUV/MLV | Liposome diameter [nm] | $T_m$ [° C.] | Surface charge | Medium | $P_{max}$ [atm] | Relative efficiency | $\mu$ Friction coefficient Lubrication efficiency |
|---|---|---|---|---|---|---|---|---|---|
| S1 | HSPC L-α-phosphatidylcholine, hydrogenated (Soy) (both surfaces coated) | SUV | 65 ± 3 | 52.5 | zwiterionic | pure water | ~120 | 5 | excellent lubrication $2 \times 10^{-5} - 10^{-4}$ |
| S2 | HSPC L-α-phosphatidylcholine, hydrogentated (Soy) (one surface only coated) | SUV | 65 ± 3 | 52.5 | zwiterionic | pure water | ~60 | 4 | very good lubrication $10^{-4}$ |
| S3 | HSPC L-α-phosphatidylcholine, hydrogenated (Soy) | SUV | 75 ± 3 | 52.5 | zwiterionic | 150 nM $NaNO_3$ | ~60 | 3 | good lubrication $2 \times 10^{-4} - 10^{-2}$ |
| S4 | HSPC: DMTAP/ 95:5 mole ratio L-α-phosphatidylcholine hydrogenated (Soy): 1,2-dimyristoyl-3-trimethylammonium-propane (chloride salt) | SUV | 65 ± 3 | 52.5 and 32 | cationic | pure water | ~30* | 4 | very good lubrication $10^{-4}$* |
| S5 | HSPC: DMTAP/ 95:5 mole ratio L-α-phosphatidylcholine hydrogenated (Soy): 1,2-dimyristoyl-3-trimethylammonium-propane (chloride salt) | SUV | 65 ± 3 | 52.5 and 32 | cationic | 150 mM $NaNO_3$ | ~60 | 4 | very good lubrication $2 \times 10^{-4} - 3 \times 10^{-3}$ |
| S6 | HSPC L-α-phosphatidylcholine, hydrogentated (Soy) | MLV | 1240 ± 570 | 52.5 | zwiterionic | pure water | ~30 | 3 | good lubrication $5 \times 10^{-4} - 7 \times 10^{-3}$ |
| S10 | DSPC 1,2-distearoyl-sn-glycero-3-phosphocholine | SUV | 65 ± 10 | 55 | zwiterionic | pure water | ~110 | 5 | Excellent lubrication $1.5 \times 10^{-4} - 7 \times 10^{-5}$ |
| S11 | DPPC 1,2-dipalmitoyl-sn-glycero-3-phosphocholine | SUV | 65 ± 10 | 41.4 | zwiterionic | pure water | ~120# | 3# | good lubrication#, $2 \times 10^{-4}$ |

*These values are for the symmetric system, where both surfaces are coated with liposome layer(s). For the asymmetric case of coated surface against a bare mica, the values show a much less efficient lubrication.
These values represent the lowest friction coefficients ($2 \times 10^{-4}$), measured at the maximal pressure (~120 atm) applied in this system (DPPC-SUV on solid mica surfaces). Because this DPPC-SUV system showed a wider diversity of values relative to the other systems described, and a tendency of μ to increase at subsequent approaches to contact point, the relative efficiency is given as 3, and the friction coefficient is described as good lubrication (rather than 5 and excellent lubrication which would be suggested by the friction-coefficient/pressure values shown).

TABLE 2

| Short name | Chemical composition | SUV/MLV | Liposome diameter [nm] | $T_m$ [° C.] | Surface charge | Medium | $P_{max}$ [atm] | Relative efficiency | $\mu$ Friction coefficient Lubrication efficiency |
|---|---|---|---|---|---|---|---|---|---|
| C7 | HSPC: DSPE PEG2000 95:5 mole ratio L-α-phosphatidylcholine hydrogenated (Soy): 1,2-distearoyl-sn-glycero-3-phosphoethanolamine-N-[amino(polyethylene glycol)-2000](ammonium salt) | SUV | ~70 | 52.5 and 75*** | Slightly negative | pure water | ~10 | 1 | poor lubrication 0.05-0.1 |
| C8 | POPC 1-palmitoyl-2-oleoyl-sn-glycero-3-phosphocholine | SUV | 66 ± 3 | −3 | zwiterionic | pure water | ~10* | 1 | poor lubrication 0.1** |

*These values are for the symmetric system, where both surfaces are coated with liposome layer(s). For the asymmetric case of coated surface against a bare mica, the values show a much less efficient lubrication.
**These values were measured upon second entries and more to the contact point. Upon first entry to contact point higher pressures of ~30 atm were measured, related to lower values of μ of $3 \times 10^{-3}$. These changes were related to damaging and squeezing the soft liposome layers attached on the surface.
***This value applies for DSPE with no attached PEG.

Methods of Preparation and Lubrication Measurements

Surface Force Balance (SFB): The SFB and its protocols for measuring normal and shear forces have been described in detail by Klein, J. and Kumacheva, E., Simple liquids confined to molecularly thin layers. I. Confinement-induced liquid to solid phase transitions. *J. Chem: Phys.* 108 (16), 6996(1998). Experimental runs were carried out by compressing the surfaces to progressively higher pressures, then decompressing by separating them, following which shear forces were measured on second and (in several cases) subsequent compressions at the same contact point, before moving to a different contact point. The results in each case were based on several independent experiments (different pairs of mica surfaces, different. PC-SUV batches), each with multiple contact points. All measurements were carried out at 23.5±0.5° C.

Example S1

Preparation of Liposomes in Water and Characterization Thereof

Multilamellar vesicles (MLVs) of HSPC ($M_w$=762.10 g/mol, >99% purity, from Lipoid, Ludwigshafen, Germany) were prepared by hydrating the phospholipids in pure water at 62° C. (above the HSPC gel-to-liquid crystalline phase transition temperature, $T_m$=52.5° C.). The MLVs were downsized to form SUVs at a HSPC concentration of 30 mM, by stepwise extrusion through polycarbonate membranes from 400-nm to 50-nm-pore-sizes at 65° C., using a Lipex 100 mL extruder system (Northern Lipids, Vancouver, Canada. Water used (also for the SFB experiments) was purified (Milli-Q® Gradient A10 or Barnsted NanoPure systems) to 18.2 MΩ cm resistance with total organic content levels of 3-4 ppb (Milli-Q) or <ca.1 ppb (Barnstead). The pH of the water was 5.8 due to ions leached from glassware and dissolved atmospheric $CO_2$. Liposomes were characterized for size distribution by dynamic light scattering using an ALV-NIBS High Performance Particle Sizer (Langen, Germany) at scattering angle of 173°. Over 98% of the freshly-prepared liposomes were 65±3 nm in diameter.

Coating of solid mica surfaces with liposomes prepared according to Example S1: Freshly cleaved, atomically smooth mica surfaces were incubated for 1.5-2 hours at 23±2° C., in a dispersion consisting of 360±10 μL of the HSPC-SUVs prepared as described in Example S1 in 10 ml water, whereon spontaneous adsorption of the liposomes took place. The surfaces were then washed (1 minutes gentle waving in excess of pure water or 5 minutes standing in pure water) to remove excess, non-adsorbed liposomes and rapidly mounted in the SFB (or taken for cryo-SEM). ensuring they remained wetted throughout. AFM (NT-MDT, Integra topography images were taken in water in tapping mode using silicon nitride tips of 3 μm height, spring-constant 0.5 N/m (Olympus, OMCL-TR800PSA). Cryo-SEM samples of HSPC-SUV-coated mica, prepared as described above, were frozen by plunging into liquid ethane and transferred to a BAF 60 freeze fracture device (Bal-Tec AG, Liechtenstein). Water was sublimed at −80° C. for 2 hrs. Samples were rotary-shadowed with 3 nm Pt at an angle of 45°. Samples were transferred to an Ultra 55 SEM (Zeiss, Germany) using a VCT 100 vacuum-cryo transfer system (Bal-Tec AG, Liechtenstein) and observed at voltages of 2.5-5 kV.

It should be noted that as a comparative example, the experiment was repeated by using a mica surface on which a positively charged Chitosan polymer was adsorbed, thereby rendering the mica surface positively (instead of negatively) charged. HSPC liposomes did not adsorb onto such a surface.

Characterization of HSPC-liposome coated Mica: Freshly cleaved mica surfaces were incubated in a dispersion of HSPC-SUV with a unimodal size distribution (diameter 65 nm), prepared as described herein, then rinsed and mounted in a surface force balance (SFB) filled with pure water. Similar liposome-coated mica surfaces were imaged using atomic force microscopy (AFM) and cryo-scanning-electron-microscopy (cryo-SEM), as shown in FIG. 1. The cryo-SEM image shows a honeycomb pattern characteristic of flattened close-packed spheres, overlaid by a loose, sparse layer of individual liposomes, which were not fully removed by the rinsing following the incubation. The AFM image (inset) shows that the liposomes are flattened by the adsorption from their unperturbed dispersion diameter to ca. 20 nm.

Lubrication: Normal and shear forces, $F_n(D)$ and $F_s(v_s, D)$ respectively, between the interacting, liposome-coated mica surfaces as a function of their closest separation D and sliding velocity $v_s$, were determined in the SFB. $F_n(D)$ profiles are shown in FIG. 2. At large separations the forces decayed exponentially with D, and are attributed to double-layer electrostatic repulsions arising from the residual charge on the interacting surfaces.

The shear or frictional forces $F_s$ transmitted between the surfaces as they were made to slide past each other were determined at different compressions (mean pressures $P=(F_n/A)$ where A is the measured contact area, up to ca. 12 MPa); sliding amplitudes $\Delta x_0$ (up to ca. 1 μm); and sliding velocities $v_s$ (5-2.10$^3$ nm/s). They were recorded directly as a series of shear-force vs. time traces as shown in FIG. 3. $F_s$ values at all pressures, shear amplitudes and shear velocities studied were constant throughout a given trace, indicating the stability of the lubricating layers over the range of tested parameters.

The $F_s$ vs. $F_n$ results are summarized in FIGS. 4A and 4B. The frictional forces on a first approach of the surfaces, empty symbols in the inset to FIG. 4A, correspond to friction coefficients $\mu=(\partial F_s/\partial F_n)$ in the range $\mu=(2\times10^{-3}\text{-}5\times10^{-4})$ as the normal pressure increases to ca. 6 MPa. These forces, however, are systematically much smaller, at similar pressures, on a second and subsequent compressions at a given contact point, as shown by the solid symbols in the main FIG. 4A (and inset), becoming lower than the noise level of the SFB up to pressures of ca. 1 MPa. At higher loads the shear forces reveal extremely low friction coefficients, down to $\mu=(2\times10^{-5})$, as shown by the dashed lines in FIG. 4A, up to the highest mean pressures attained in this study, P=ca. 12 MPa. The dependence of $F_s$ on $V_s$ is shown in FIG. 4B for different high pressures, indicating, within the scatter, little variation in friction over nearly 3 orders-of-magnitude in sliding velocities (5-2.10$^3$ nm/s).

The strong reproducibility of the friction, on multiple approaches at the same contact point suggests that the HSPC-SUVs retain their structural integrity up to the highest pressures tested, even under shear. The limiting separation at $D_{hw}$=21±2 nm at the highest compressions corresponds to a thickness of some 4 bilayers of the HSPC phospholipids, consistent with two essentially flattened SUV layers.

Example 2

Coating of One Solid Mica Surface with Liposomes

In another experiment the interactions between a bare mica surface and a mica surface coated with SUV HSPC liposomes prepared in pure water (according to Example S1) was tested. In this experiment SUV-HSPC liposomes were adsorbed to a single mica sheet which was brought into contact with an atomically smooth mica sheet, while measuring the force as a function of the distance between the surfaces. Two different surface coverages were obtained due to a different washing technique after the adsorption procedure. A more vigorous wash which left large areas of bare mica—is referred as 'b', and a gentle wash procedure that lead to a dense surface is referred as 'a'.

This system showed, for high surface coverage, very good levels of lubrication, $\mu \approx 10^{-4}$, up to pressures of ca. 6 Mpa, and for the low surface coverage (namely after extensive washings) showed high friction at pressures higher than 1 MPa.

Example S3

Preparation of Liposomes in Salt Environment

The same process described above (S1/S2) was repeated with the modification that the liposomes were prepared in 150 mM $NaNO_3$ (Fluka, >99.999% purity) rather than in pure water. Liposomes were characterized for size distribution by dynamic light scattering using an ALV-NIBS High Performance Particle Sizer (Langen, Germany) at a scattering angle of 173°. Over 98% of the freshly-prepared liposomes were 75±3 nm in diameter.
Coating of Solid Mica Surfaces with Liposomes Prepared by Example S3:

HSPC-SUV were adsorbed on atomically smooth mica surface by placing freshly cleaved mica in 10 ml 150 mM $NaNO_3$ and then adding 360±10 µL of the liposome dispersion (of concentration of 30 mM) for 1.5-2 hours of incubation. Then mica surfaces were washed to remove excess, non-adsorbed liposomes by placing the adsorbed surfaces in a beaker filled with 150 mM $NaNO_3$ for a few minutes along with a delicate shake motion. All preparations were done in a laminar hood to prevent contamination.
Results As summarized in Table 1, good lubrication was obtained between two surfaces coated with liposomes prepared as above, with $\mu = 2 \times 10^{-4} - 10^{-2}$ at pressures up to 60 atmospheres.

Example S4

Preparation of HSPC/DMTAP Liposome Mixtures in Pure Water Environment

Hydrogenated Soy phosphocholine (HSPC, Mw=762.10 g/mol, Tm 52.50° C., >99% purity) was purchased from Lipoid (Ludwigshafen, Germany). 1,2-ditetradecanoyl-3-trimethylammonium-propane (chloride salt) (DMTAP, Mw=590.361 g/mol) was purchased from Avanti Polar Lipids, Inc. (Alabaster, Ala. USA).

A mixture of HSPC and DMTAP (in a 95:5 mole ratio) was dissolved in hot ethanol to a concentration of 0.45 w/v. This solution was injected into pure water at temperature of 62° C. (above the gel-to-liquid crystalline phase transition temperature, Tm, of HSPC, 52.5° C.) in order to hydrate the lipids and form a dispersion of multilamellar liposomes, MLV at final concentration of 30 mM phospholipids (PL). Water was treated with a Barnstead Nanopure system. The resistance of water was 18.2 MΩ cm with total organic compound (TOC)<ca.1 ppb (Barnstead). MLV were downsized to form small unilamellar vesicles (SUV), 65 nm in diameter, at a concentration of 15 mM, by stepwise extrusion through polycarbonate membranes starting with a 400-nm and ending with 50-nm-pore-size membrane, using a Lipex 100 mL extruder system (Northern Lipids, Vancouver, Canada).

Liposomes were characterized for size distribution by dynamic light scattering using an ALV-NIBS High Performance Particle Sizer (Langen, Germany) at a scattering angle of 173°. Over 98% of the freshly-prepared liposomes were 75±3 nm in diameter.

The zeta potential of liposomes in pure water was 36.5 mV.
Coating of Solid Mica Surfaces with Liposomes Prepared by Example S4:

Cryo-SEM image of a mica surface covered with SUV HSPC/DMTAP liposomes in pure water showed that liposome adsorbed on a mica surface in not close-packed coverage.

Normal force measurements between two opposing layers of HSPC/DMTAP in water revealed increased long range repulsion starting from D=250±50 nm down to a hard wall separation of 10±2 nm. Normal force measurements between one mica surface covered with HSPC/DMTAP liposomes against bare mica show repulsion which starts from D=150±75 nm down to a hard wall separation of 6±1 nm.

On second approach to the same contact point a higher normal force was measured for the same surface separation D. In the HSPC/DMTAP vs. bare mica system, a jump out was observed.

Shear measurements of 2 HSPC/DMTAP coated mica surfaces in pure water show no response to shear up to pressures of 25±6 atm. A shear trace test demonstrated the low Fs as P<~30 atm.

Shear measurements of 1 HSPC/DMTAP coated surface vs. bare mica in pure water showed rigid coupling already in pressures of ~10 atm.

Fs vs. Fn for 1 HSPC/DMTAP coated surface vs. bare mica gave effective friction coefficient of 0.035, and for two-HSPC/DMTAP coated surfaces gave effective friction coefficient of 0.0001 for the higher load region.

Example S5

Preparation of HSPC/DMTAP Liposome Mixtures in Salt Environment

The same process described above (S4) was repeated with the modification that the liposomes were prepared in 150 mM $NaNO_3$ (Fluka, >99.999% purity) rather than in pure water using four dialysis steps at 4° C.

Liposomes were characterized for size distribution by dynamic light scattering using an ALV-NIBS High Performance Particle Sizer (Langen, Germany) at a scattering angle of 173°. Over 98% of the freshly-prepared liposomes were 61.9 nm in diameter.

The zeta potential of liposomes was 4.18 mV after replacing the external medium with 150 mM $NaNO_3$.
Coating of Solid Mica Surfaces with Liposomes Prepared by Example S5:

HSPC/DMTAP SUV were adsorbed on atomically smooth mica surface by placing freshly cleaved mica in 10 ml 150 mM $NaNO_3$ salt solution and then adding 720±20 µL of the liposome dispersion for 1 hour of incubation. After 1 hour the mica surfaces were placed in 400 ml beaker of 150 mM $NaNO_3$ for 1-2 minutes in order to remove excess, non-adsorbed liposomes.

Cryo-SEM samples (mica surfaces covered with HSPC: DMTAP 95:5 liposomes) were prepared as described above, with additional rinsing step by placing the sample in pure water for few seconds in order to remove salt. Samples were frozen by plunging into liquid ethane and transferred to a BAF 60 freeze fracture device (BAl-Tec AG, Liechtenstein). Water was sublimed in the BAF 60 at a temperature of −100 degrees for 1 hour. Pt cover of the samples by rotary shadowing of 1.5 nm followed by 1.5 nm of Pt in an angle of 45 degrees. Samples were transferred to an Ultra 55 SEM (Zeiss, Germany) using a VCT 100 vacuum-cryo transfer system (Bal-Tec AG, Liechtenstein) and observed at voltages of 2.5 to 5 kV. Cryo-SEM imaging of the liposomes showed that the HSPC/DMTAP liposomes indeed adsorbed onto the mica to form a dense carpet on the surface. The liposomes did not fuse but remained separated from one another, where each liposome had a mean diameter of ca. 64 nm (in the range of 35 nm to 92 nm).

Normal force profiles between the two mica surfaces covered with HSPC/DMTAP liposomes immersed in 150 mM $NaNO_3$ solution showed no interaction down to surface separation of 90±30 nm. Then, repulsion force evolves increasing rapidly as surfaces are forced to approach one another. At the highest normalized loads of 2 N/m corresponding to pressures of ca. 6 MPa the surfaces reached hard wall separation of 31±2 nm. On the second approach to the same contact point, a higher repulsion force was measured for a given surface separation D.

The effective, friction coefficient $\mu = \partial Fs / \partial Fn$ was calculated to be in the range of $\mu = 3 \times 10^{-3} - 2 \times 10^{-4}$ as the normal pressure increased to about 6 MPa.

Example S6

Preparation Of MLV HSPC Liposomes in Water, Characterization thereof and Solid Surfaces Coated by it Hydrogenated Soy phosphocholine (HSPC, Mw=762.10 g/mol, Tm 52.50° C., >99% purity) was purchased from Lipoid (Ludwigshafen, Germany). 0.9145 gr HSPC were dissolved in hot ethanol to a concentration of 0.45 w/v. This solution was injected into pure water at temperature of 62° C. (above the gel-to-liquid crystalline phase transition temperature, Tm, of HSPC, 52.5° C.) in order to hydrate the lipids and form a 40 ml dispersion of multilamellar liposomes, MLV at final concentration of 30 mM phospholipids (PL). Water was treated with a Barnstead Nanopure system. The resistance of water was 18.2 MΩ cm with total organic compound (TOC)<ca.1 ppb (Barnstead). MLV HSPC mean radius size of 1.24±0.57 µm was measured with particle size analyzer LS 13 320 equipped with the PIDS unit which can determine particle size at the range of 40 nm to 2.0 mm (Beckman Coulter).

Normal force measurements between mica surface covered with HSPC MLVs liposomes in opposing to a bare mica surface in pure water reveal repulsion starting from D=1250±250 nm. The measured normal force in the second approach to a contact point was lower then what was measured on the first approach to the point for a given surface separation D. Contact hard wall position value was found to be around 70 nm. However, during shear this value was reduced—after 12 minutes of shear the hard wall value was reduced by 3.5 nm.

Shear force measurements between a mica surface covered with HSPC MLVs liposomes in opposing to a bare mica surface in pure water at different surface separation D and applied normal force (pressure) show that a similar shear force was measured during the first approach to a contact point and on during the second approach.

From the plot of Fs vs. Fn the effective friction coefficient µ was deduced to be in the range of $\mu = 7 \times 10^{-3}$ to $5 \times 10^{-4}$, for both first and second approaches as pressures are up to ~30 atm.

Example S10

Preparation of SUV-DSPC Liposomes in Pure Water, Characterization thereof and Solid Surfaces Coated by it MLV-DSPC liposomes (DSPC, Mw=790.145 g/mol, Tm 55° C., >99% purity, from Lipoid, Ludwigshafen, Germany) were prepared by hydrating the phospholipids in pure water at around 65° C. (above the gel-to-liquid crystalline phase transition temperature). The MLVs were downsized to form SUVs at a final concentration of 15 mM, by stepwise extrusion through polycarbonate membranes from 400-nm to 50-nm-pore-sizes at 65° C., using a Lipex 100 mL extruder system (Northern Lipids, Vancouver, Canada. Water used (also for the SFB experiments) was purified (Barnsted NanoPure systems or milli-Q gradient A10) to 18.2 MΩ cm resistance with total organic content levels of 3-4 ppb (Milli-Q) or <ca.1 ppb (Barnstead). The pH of the water was 5.8 due to ions leached from glassware and dissolved atmospheric $CO_2$. Liposomes were characterized for size distribution by dynamic light scattering using an ALV-NIBS High Performance Particle Size (Langen, Germany) at a scattering angle of 173°. Over 98% of the freshly-prepared liposomes were 65±10 nm in diameter. The normal force profiles were similar in range and magnitude to those described for HSPC-SUV in example S1 above (e.g. FIG. 2). The shear traces and resulting load vs. friction data are shown in FIGS. 5A and 5B, revealing excellent lubrication up to high pressures (>100 atms). Cryo-SEM micrographs of the DSPC-SUV on mica revealed close-packed layers on the surface.

Example S11

Preparation of SUV-DPPC Liposomes in Pure Water, Characterization thereof and Solid Surfaces Coated by it MLV-DPPC liposomes (DPPC, Mw=734.1, Tm 41.4° C., >99% purity, from Lipoid, Ludwigshafen, Germany) were prepared by hydrating the phospholipids in pure water at 55° C. (above the gel-to-liquid crystalline phase transition temperature). The MLVs were downsized to form SUVs at a final concentration of 15 mM, by stepwise extrusion through polycarbonate membranes from 400-nm to 50-nm-pore-sizes at around 60° C., using a Lipex 100 mL extruder system (Northern Lipids, Vancouver, Canada. Water used (also for the SFB experiments) was purified (Barnsted NanoPure systems or milli-Q gradient A10) to 18.2 MΩ cm resistance with total organic content levels of 3-4 ppb (Milli-Q) or <ca.1 ppb (Barnstead). The pH of the water was 5.8 due to ions leached from glassware and dissolved atmospheric $CO_2$. Liposomes were characterized for size distribution by dynamic light scattering using an ALV-NIBS High Performance Particle Size (Langen, Germany) at a scattering angle of 173°. Over 98% of the freshly-prepared liposomes were 65±10 nm in diameter. Normal force profiles on first approach set on at a range and of magnitude similar, though somewhat smaller, to those for HSPC-SUV (FIG. 2), and shear traces at some of these points revealed very low friction (CoF down to $2\times10^{-4}$ or even lower) at pressures up to 120 atms (12 MPa). The distance of closest approach at these highest pressures and shear were in the range 10-15 nm. On subsequent approaches at a given contact point the pressures that could be applied, prior to higher friction setting on, were significantly lower. The overall picture therefore was that despite the optimal low-friction, high-pressure values, in View of the range of results, the DPPC-SUV liposomes on solid surfaces were designated good, level 3 (rather than excellent, level 5) lubricants, as explained following Table 1 for S11.

These results relate to good to excellent boundary lubrication of solid surfaces by two different SUV gel-phase liposomes additional to the HSPC, consisting of DPPC (S11), with Tm=41.4° C., and of DSPC (S10) which has a Tm=55° C. FIGS. 5A and 5B show the friction traces and the friction vs. load plot for the DSPC-SUV liposome and indicate the very low friction coefficient even up to 100 or more atms, at around room temperature (Troom=25° C., clearly much lower than Tm). In addition, there are traces for the DSPC-SUV that show clearly that the friction after very long sliding—an hour or so—remains very low, indicating that wear is very low: this is a qualitatively new and very important indication, showing that even after thousands of back-and-forth cycles the lubricating layer retains its integrity and efficiency.

Comparative Examples

Comparative Example C7

Preparation of SUV HSPC/PEG Liposome Mixtures in Water, Characterization Thereof and Solid Surfaces Coated by it SUV HSPC/PEG liposome mixtures in water were prepared as a comparative example, since the PEG external head groups have an end-to-end radius which is larger than 1 nm (being 4 nm). The HSPC/PEG liposomes were prepared and characterized as described in *Langmuir* 21, 2560 (2005).

Cryo-SEM images of mica surfaces covered with HSPC/PEG liposomes show liposomes indeed adsorbed onto mica surface. Normal force profiles between two SUV HSPC/PEG coated mica surfaces across pure water show repulsion from ~100 nm. Hard wall of 10±4 nm was reached by increasing the normal load. At some contact points at higher pressures of more than ~21 atm, the adsorbed layers were removed from the internal gap, and a surface separation of D=+0.8 nm.

Shear traces show that Fs increase along with the rise in pressure such that for pressure of ~25±5 atm., the two surfaces no longer slided one past the other but they move together in tandem so that no further sliding between them occurred. The effective friction coefficient up to that point was in the range of 0.05-0.03.

Comparative Example C8

Preparation of SUV POPC Liposomes in Water, Characterization thereof and Solid Surfaces Coated by it SUV POPC liposomes in water were prepared as a comparative example, since the obtained liposome has a Tm which is smaller than the measuring temperature, being smaller than about 15° C. (being −3° C.). 1-palmitoyl-2-oleoyl-sn-glycero-3-phosphocholine (POPC, Mw=760.076 g/mol, Tm −3° C., >99% purity) was purchased from Lipoid (Ludwigshafen, Germany). 0.456 gr POPC were dissolved in hot ethanol to a concentration of 0.45 w/v. This solution was injected into pure water at temperature of 250° C. (above the gel-to-liquid crystalline phase transition temperature, Tm, of POPC, −3° C.) in order to hydrate the lipids and form a dispersion of multilamellar liposomes, MLV at final concentration of 30 mM phospholipids (PL). Water was treated with a Barnstead Nanopure system. The resistance of water was 18.2 MΩ cm with total organic compound (TOC) <ca.1 ppb (Barnstead). MLV were downsized to form small unilamellar vesicles (SUV), ca. 68 nm in diameter, by stepwise extrusion through polycarbonate membranes starting with a 400-nm and ending with 50-nm-pore-size membrane, using a Lipex 100 mL extruder system (Northern Lipids, Vancouver, Canada).

Liposomes were characterized for size distribution by dynamic light scattering using Malvern Zetasizer—nano series (Malvern Instrument Limited-UK) at a scattering angle of 173°. 100% of the liposomes were 68.8 nm in diameter.

Normal force measurements between two opposing layers of POPC in pure water revealed repulsion starting from D=100±20 nm down to a hard wall separation of 10.5±1 nm. Upon separation and reentering the contact point the normal force profile is shifted in the repulsion region such that for a given surface separation D, Fn/R is higher on the second approach then the first approach. A jump out from a distance of Dj=17.3±3.5 nm was observed while separating the two surfaces from contact. The surface tension r was deduced from the jump out separation, distance to be T=6.1±3.1 mN/m both on first and second separation from the contact point.

Shear measurements were preformed between two opposing adsorbed layers of POPC at different surface separation D and applied normal force (pressure). Traces show that the shear force is higher upon second approach to a contact point then the first approach. On first approach the friction force remains low for pressures values of P<~25 atm; on second approach the corresponding pressure to reach such low friction force values are much lower P<~10 atm.

During shear, it occurred that the measured friction force increased dramatically from a low friction force that has a sliding trace shape, into a rigid coupling of the two surfaces of a triangular trace shape, which means the friction was so high that they were no longer sliding.

From the plot of Fs vs. Fn it can be deduced that the effective friction coefficient μ for the first approach is $\mu=3\times10^{-3}$, but from the second approach the friction coefficient increased to $\mu=1\times10^{-1}$.

The friction was measured between mica surfaces each coated with a layer of POPC SUVs (which, unlike the similarly-sized HSPC-SUVs, are in the liquid-crystalline phase at room temperature, Tm(POPC)=−3° C.). It was found that such layers provided poor lubrication (friction coefficients up to μ=0.1) at pressures of just 1 MPa. Force profiles suggested that at higher pressures the POPC-SUVs had collapsed and were being partly squeezed out from between the surfaces, attributed to the lower rigidity (higher fluidity) of these liquid-crystalline-phase vesicles, resulting in a less stable phosphocholine lubricating layer at high pressures.

Example T1

Testing in Biological Systems

Materials and Methods

Lipids. Table 1 describes the lipids (>98% pure) used in this experiment.

Hyaluronic Acid (HA). A linear heteropolysaccharide with repeating 3-O-(β-D-glucuronido)-N-acetyl-D-glucosamine units linked by (β1-4) hexosaminidic bonds, sourced from rooster combs, having an average molecular weight of $(1-4)\times10^6$ (Sigma) was dissolved in histidine buffer (HB) to a concentration of 5 mg/ml.

Water. Water used was purified Barnsted NanoPure systems to 18.2 MΩ cm resistance with total organic content levels of <ca.1 ppb.

Liposomes. Multilamellar vesicles (MLV) composed of pure Phosphatidylcholines (PCs): POPC, DMPC and HSPC, were prepared by hydrating the lipids in at least 5° C. above the lipid $T_M$. To get small unilamellar vesicles (SUV, <100 nm), MLVs were downsized by stepwise extrusion through polycarbonate membranes starting with a 400-nm and ending with 50-nm-pore-size membrane, using a Lipex 100 mL extruder system (Northern Lipids, Vancouver, Canada), heated at least 5° C. above the lipid $T_M$. The following liposomes suspensions were used: MLVs liposomes concentration was of 130±10 mM, SUVs liposomes concentration was of 35±5 mM.

Cartilage. Articular cartilage from freshly slaughtered and healthy bovine was used for friction tests. Specimens of cartilage (approximately thickness of 3-4 mm) were removed from the surface using a scalpel. Samples were kept at −20° C. until used. For each test two samples were glued: one on the lower surface and the other on the upper surface. Size of the lower surface was ~0.8 cm$^2$ and size of the upper surface was 0.14±0.02 cm$^2$. The cartilage samples were glued to their holders using a cyanoacrylate-based glue.

Friction Testing. Friction testing was carried out using a CETR© tribometer, UMT model with high sensor which enables high normal loads. The system configuration was of a cartilage on a cartilage setup, in which two samples of bovine cartilage are immersed in HB, saline (0.9% w/v) or in synovial fluid (SF, obtained from the fresh bovine joints). The cartilage samples were subjected to relative sliding over a wide range of loads of 1 to 12 kg (10 to 120 N), equivalent to physiological pressures in joints (0.73±0.1 MPa to 8.75±1.25 MPa). The testing parameters were the following: Sliding velocity of 1 mm/sec, sliding amplitude of 1.5 mm and dwell time of 5 sec. Experiments were at room temperature (ca. 25±1 C)

The static friction coefficient is obtained from the maximum value from the shear trace, and the kinetic friction coefficient is calculated as the average value at the sliding region. The data summaries are based on the mean of 2-3 independent experiments (i.e. 2-3 fresh pairs of cartilage surfaces) in each case, except for the synovial fluid control (1 experiment), and 40. back-and-forth cycles per measurement. The cartilage surfaces were incubated for 30 mins in the liposome solutions prior to friction measurements.

| Short name | Chemical name | MW | Phase transition temperature $(T_m)$, ° C. |
|---|---|---|---|
| POPC | 1-palmitoyl-2-oleoyl-sn-glycero-3-phosphocholine | 760.1 | -3 |
| DMPC | 1,2-dialyristoyl-sn-glycero-3-phosphocholine | 677.9 | 23.2 |
| HSPC | hydrogenated soybean phosphocholine | 762.1 | 52.5 |

The results of the lubrication experiments are shown in FIGS. 6A-B and 7A-B. The trends of the friction data in the experiments with the liposomes were striking and very much in line with the earlier examples described in Tables 1 and 2 where the gel-phase liposomes were better lubricants at high pressures. At the lower pressures, around 2.2 MPa pressure (30N load), the dynamic friction coefficients of all three systems (DMPC-MLV, POP-CMLV and HSPC-MLV) were similar to each other, in the range CoF μ=0.032±0.007, with the DMPC-MLV at the lower part of this range and the POPC-MLV at the higher part of this range. At the highest pressures, around 8.8 MPa (which is comparable to the pressures in human hips and knees), the values of the friction coefficients diverge significantly: HSPC-MLV (gel-phase at the temperature of the measurement) now had significantly lower CoF □≈0.02, compared with CoF □≈0.04 for the DMPC-MLV (liquid crystalline phase at the temperature of the measurements) and □≈0.085 for the POPC-MLV (liquid crystalline phase at the temperature of measurements).

In the Figures:

FIG. 1: Cryo-SEM image of the HSPC-SUV adsorbed on freshly cleaved mica as described in Methods section;

FIG. 2: Part A: Normal force Fn vs. surface-separation D profiles between interacting HSPC-SUV coated mica surfaces. Profiles are normalized as Fn/R in the Derjaguin approximation, by the mica curvature radius R≈1 cm; the black line is the far-field force variation predicted by the DLVO model, $(Fn(D)/R)=128 pck_BT k^{-1} \tan h^2 (ey0//k_BT) \exp(-kD)$, where c is the effective ion concentration, $k_B$ and T are Boltzmann's constant and the absolute temperature, $k^{-1}$ is the Debye screening length, e is the electronic charge and y0 the effective electrostatic potential, derived from the far-field profile, at the interacting surfaces (taken as the outer opposing liposome surfaces). For the best fit shown, $k^{-1}=66$ nm corresponding to $c=2.3\times10^{-5}$M of a 1:1 electrolyte, and y0=120 mV. The inset compares profiles on a first approach (full symbols) and second approach (corresponding empty symbols) from different contact positions. Part B: The flattened interference fringes shown correspond to a pressure of 10±1 MPa (arrow in part A); they provide a direct section through the contact zone (schematically shown on the right of part B), and from such fringes the contact area $A=pr^2$, and hence the mean pressure P=Fn/A, are evaluated;

FIG. 3: Typical shear (or friction) force Fs vs. time traces between HSPC-SUV coated mica surfaces taken directly from SFB;

FIG. 4A: Friction forces Fs vs. applied loads Fn between two HSPC-SUV-coated mica surfaces, based on traces such as in FIG. 3;

FIG. 4B: Friction forces $F_s$ variation with sliding velocity for different compressions (○ 74 atm; ◁ 94 atm; ■ 107 atm; ▶ 118 atm) of HSPC-SUV coated mica surfaces showing little variation within the scatter over nearly 3 decades in $v_s$.

FIG. 5A: Shear traces between two mica surfaces coated with SUV-DSPC liposomes in pure water, measured using the surface force balance showing the shear force Fs vs. time. The traces demonstrate the shear force at different surface separations under various applied pressures.

FIG. 5B: Friction force vs. the applied normal load between two SUV-DSPC coated mica surfaces, based on traces such as in 5A. The effective friction coefficient μ is calculated as μ=dFs/dFn directly from the graph, and reveal the excellent lubrication capability of such SUV-DSPC system.

Figure 1:
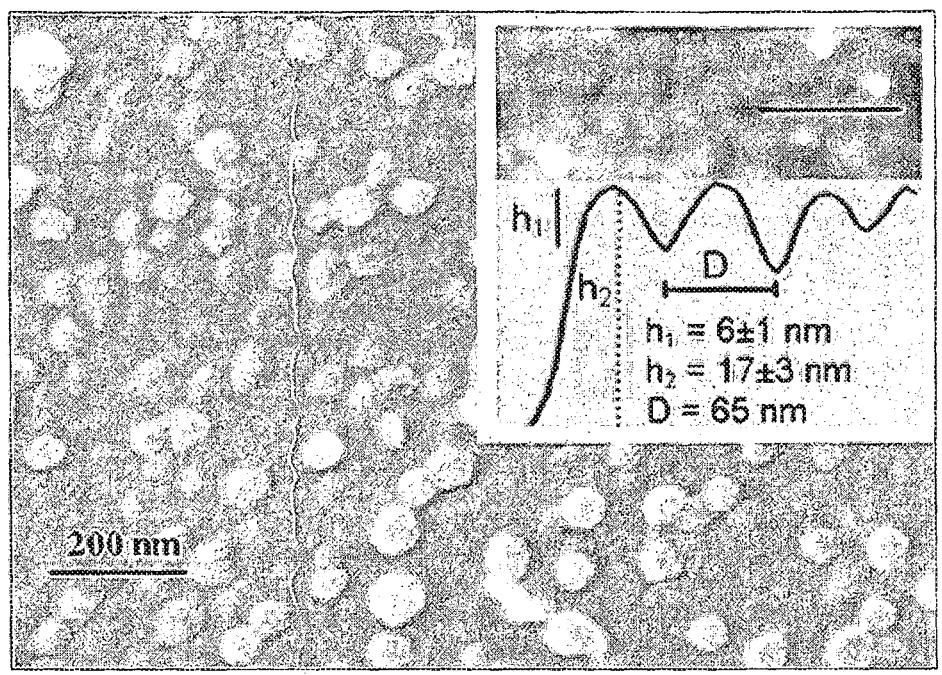
Figure 2:
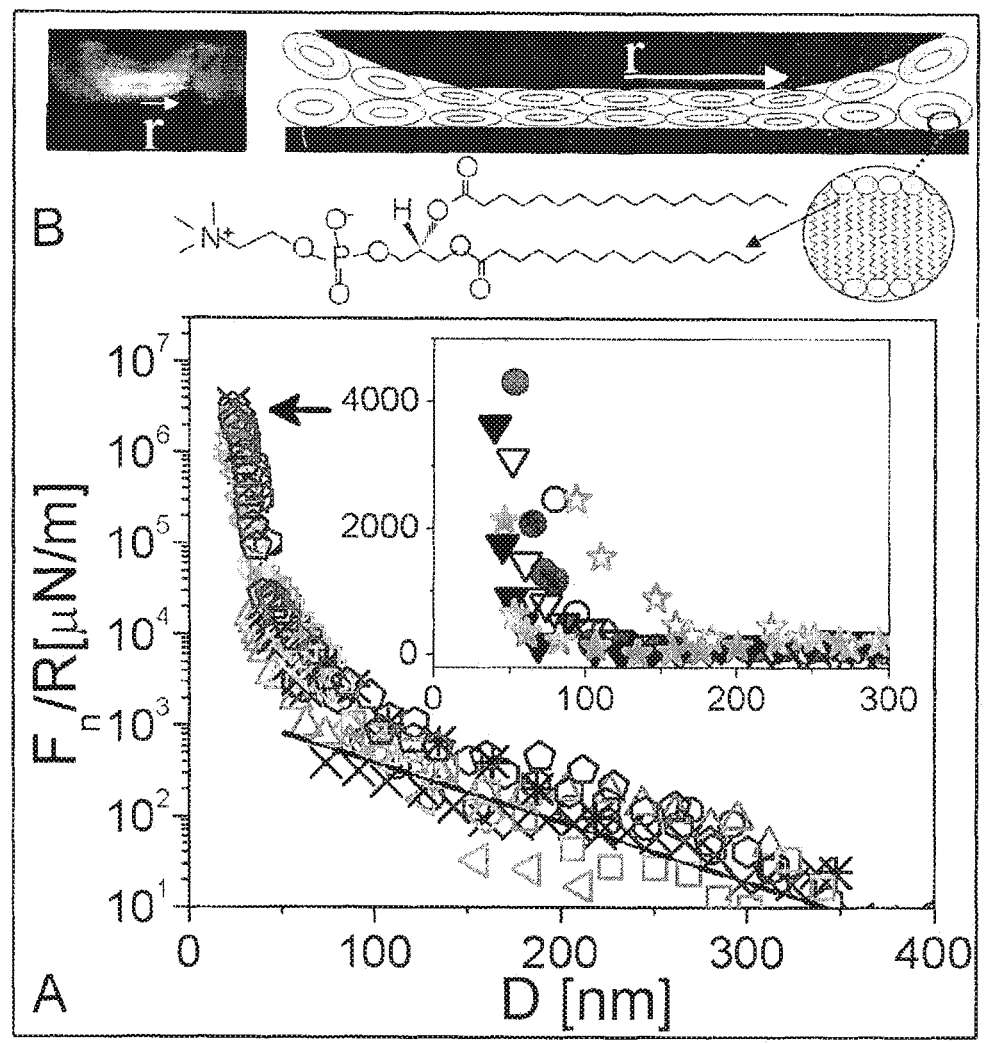
Figure 3:
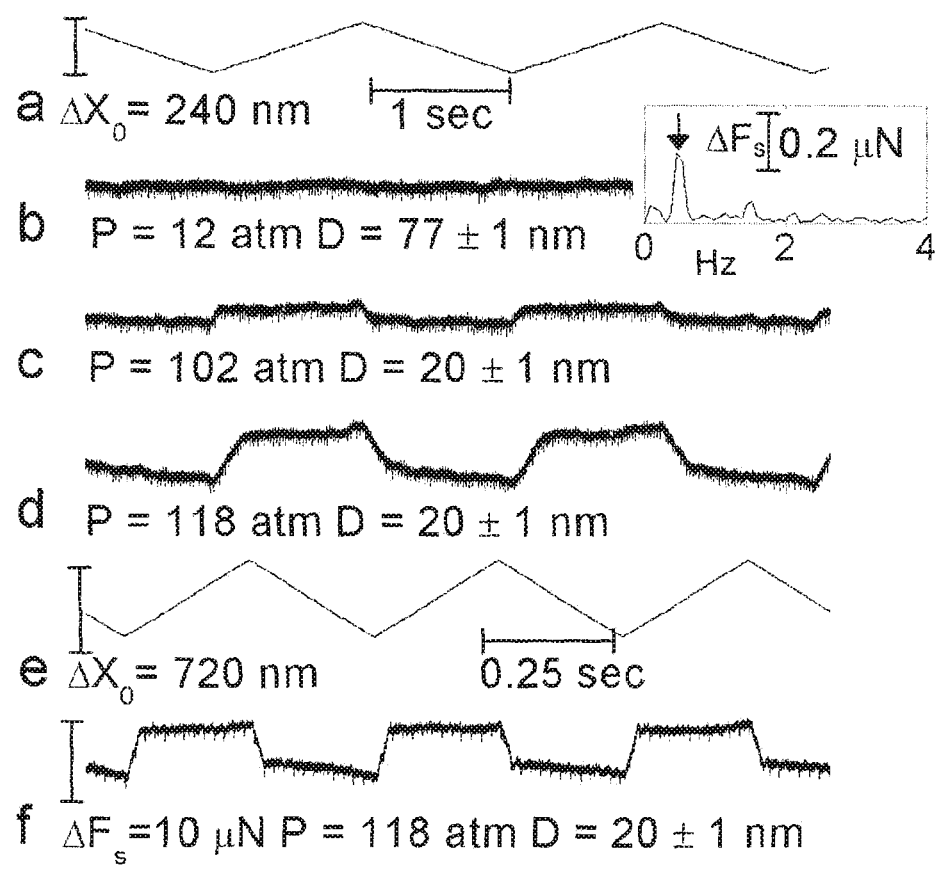
Figure 4A:
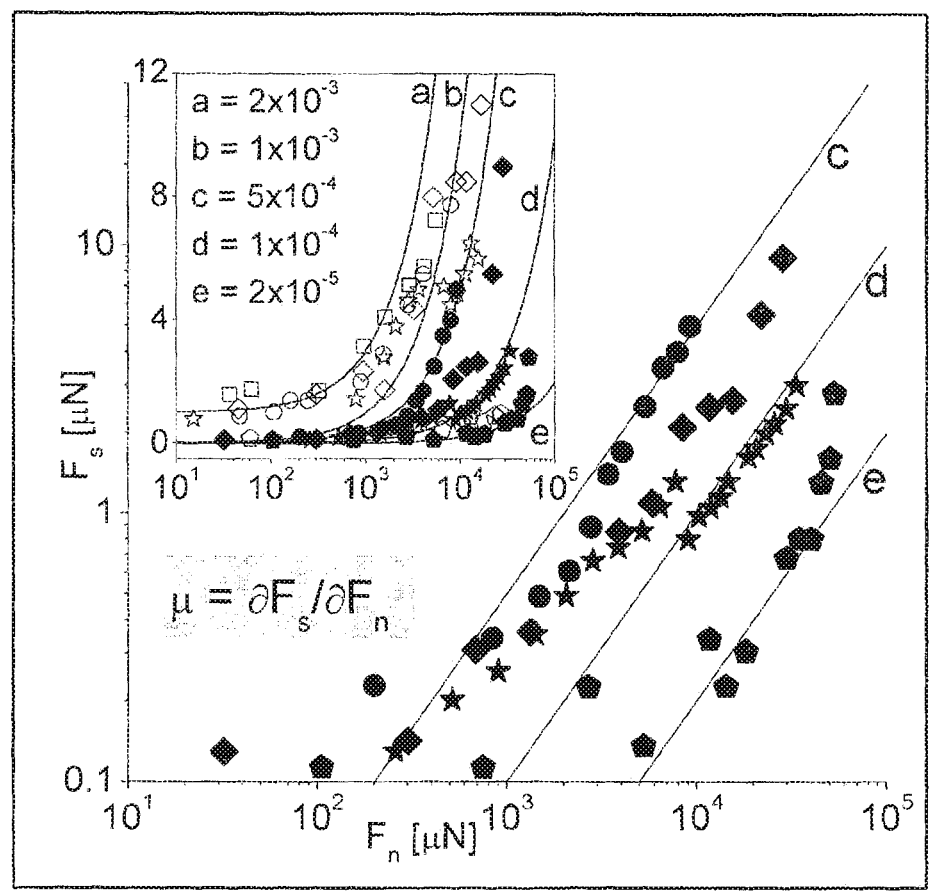
Figure 4B:
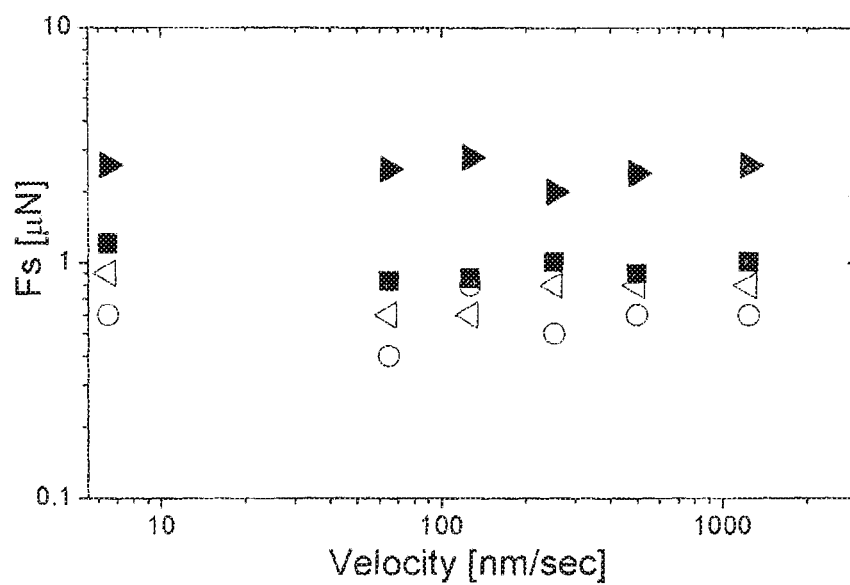
Figure 5A:
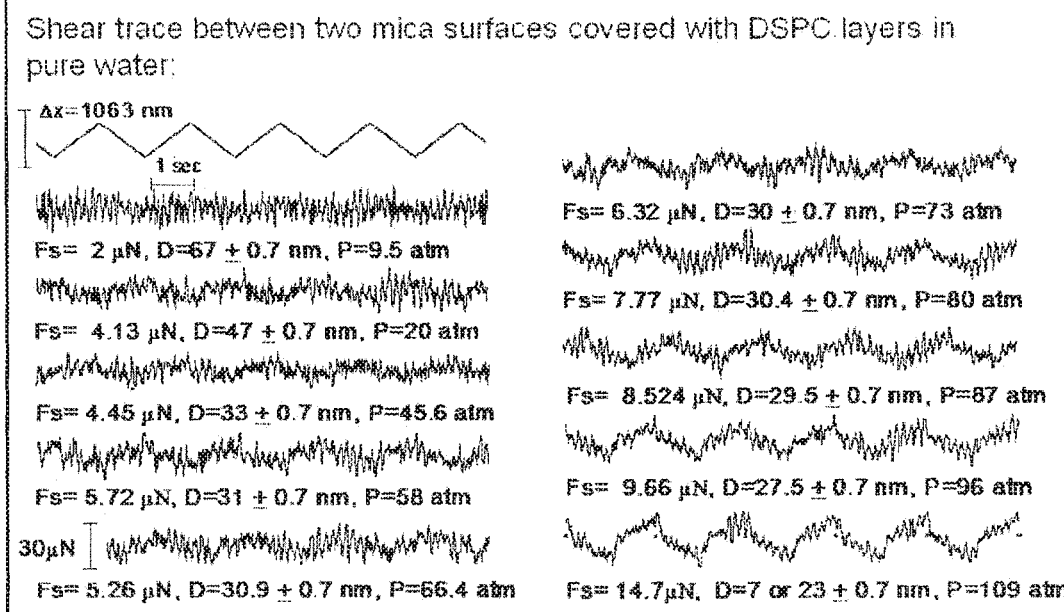
Figure 5B:
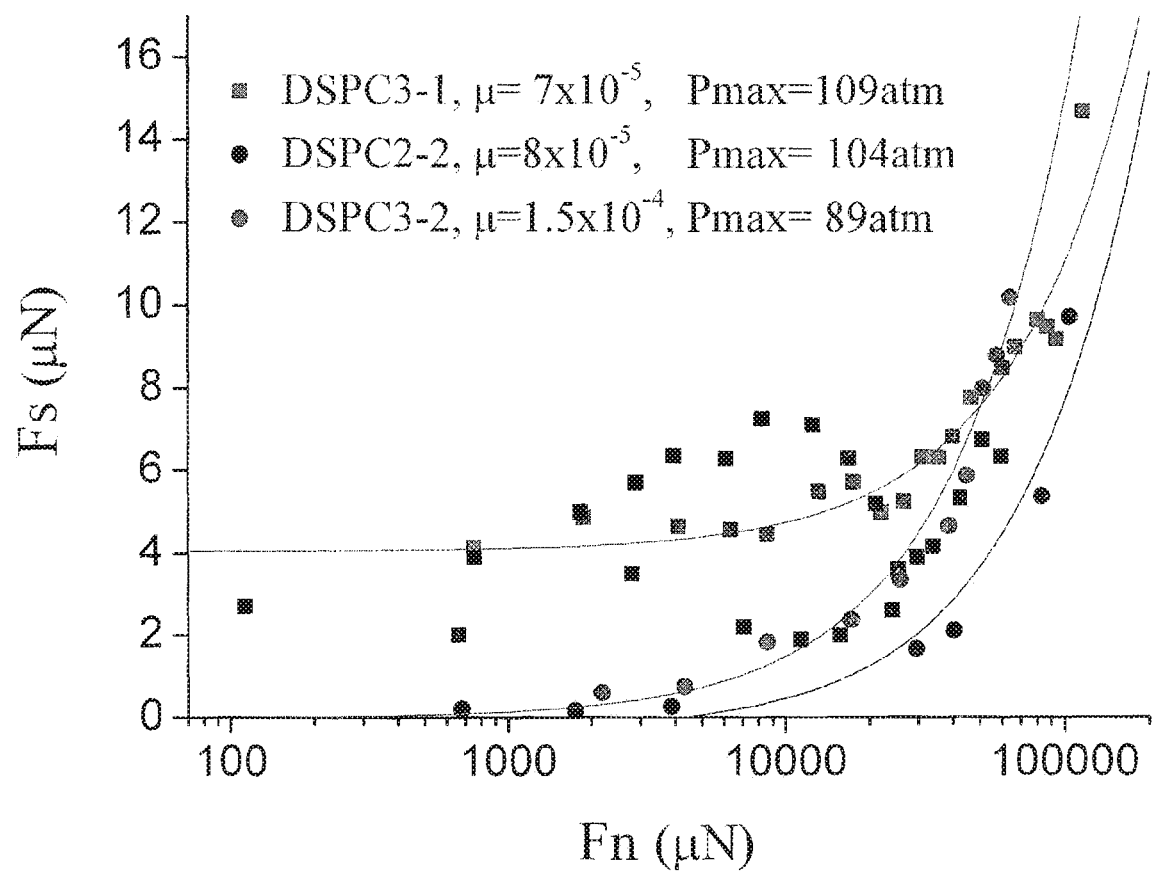
Figure 6A:
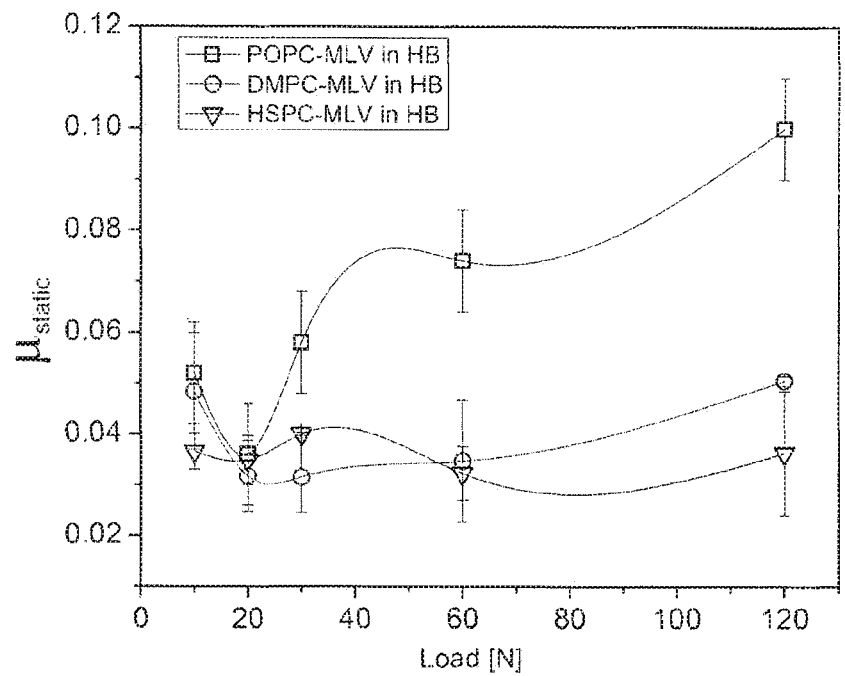
FIGS. 6A and 6B show Dynamic (6A) and Static (6B) Friction coefficients vs. load (N) according to preferred embodiments of the invention for bovine articular cartilage surfaces following incubation in HSPC-MLV, DMPC-MLV, and POPC-MLV liposome solutions in histidine buffer.
Figure 6B:
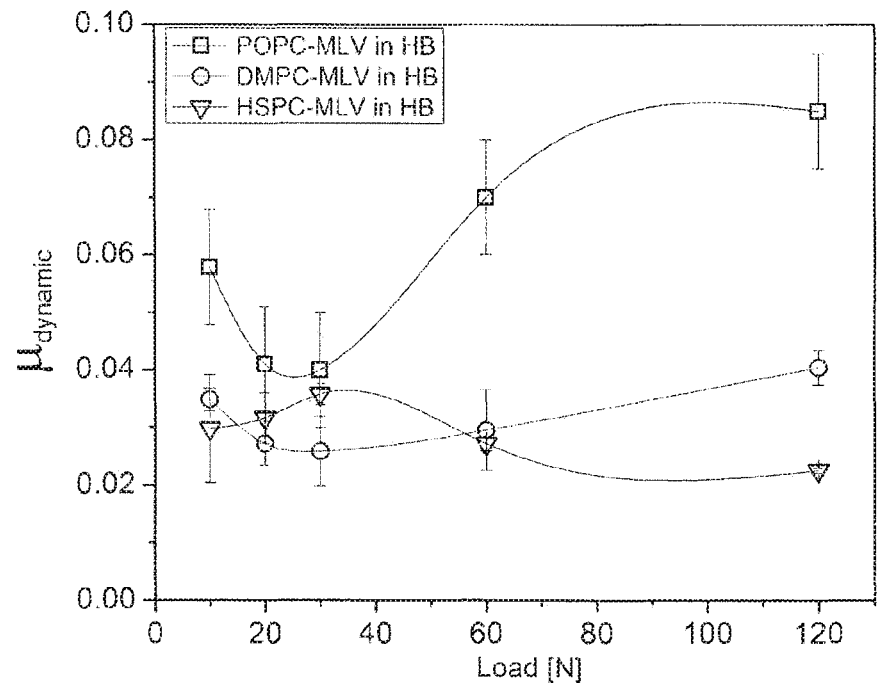
Figure 7A:
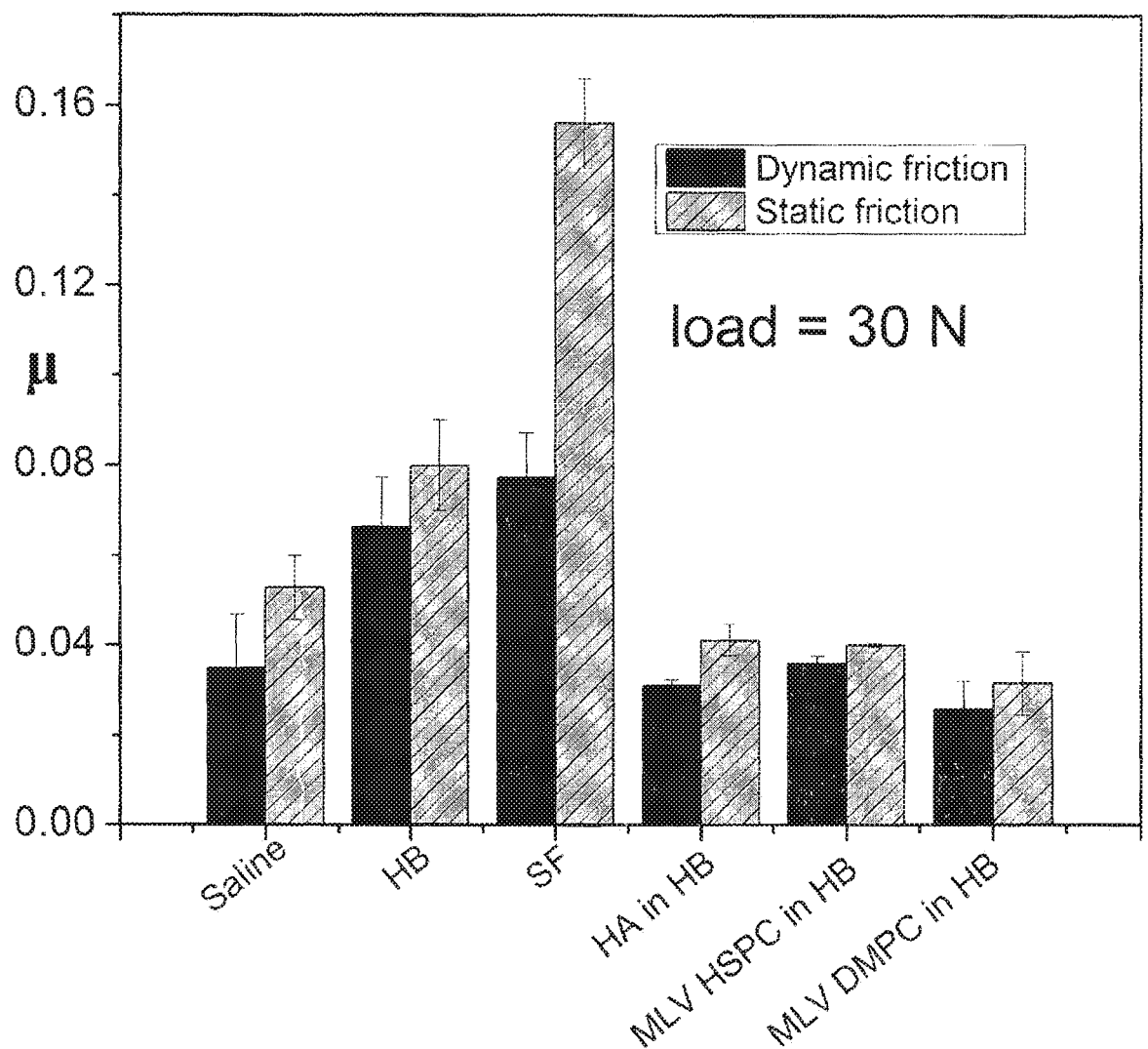
FIGS. 7A and 7B show Dynamic and Static friction coefficients for different systems (both controls and with liposomes) for a 30N load (FIG. 7A) and for a 120N load (FIG. 7B) between sliding bovine cartilage surfaces according to preferred embodiments of the invention.
Figure 7B:
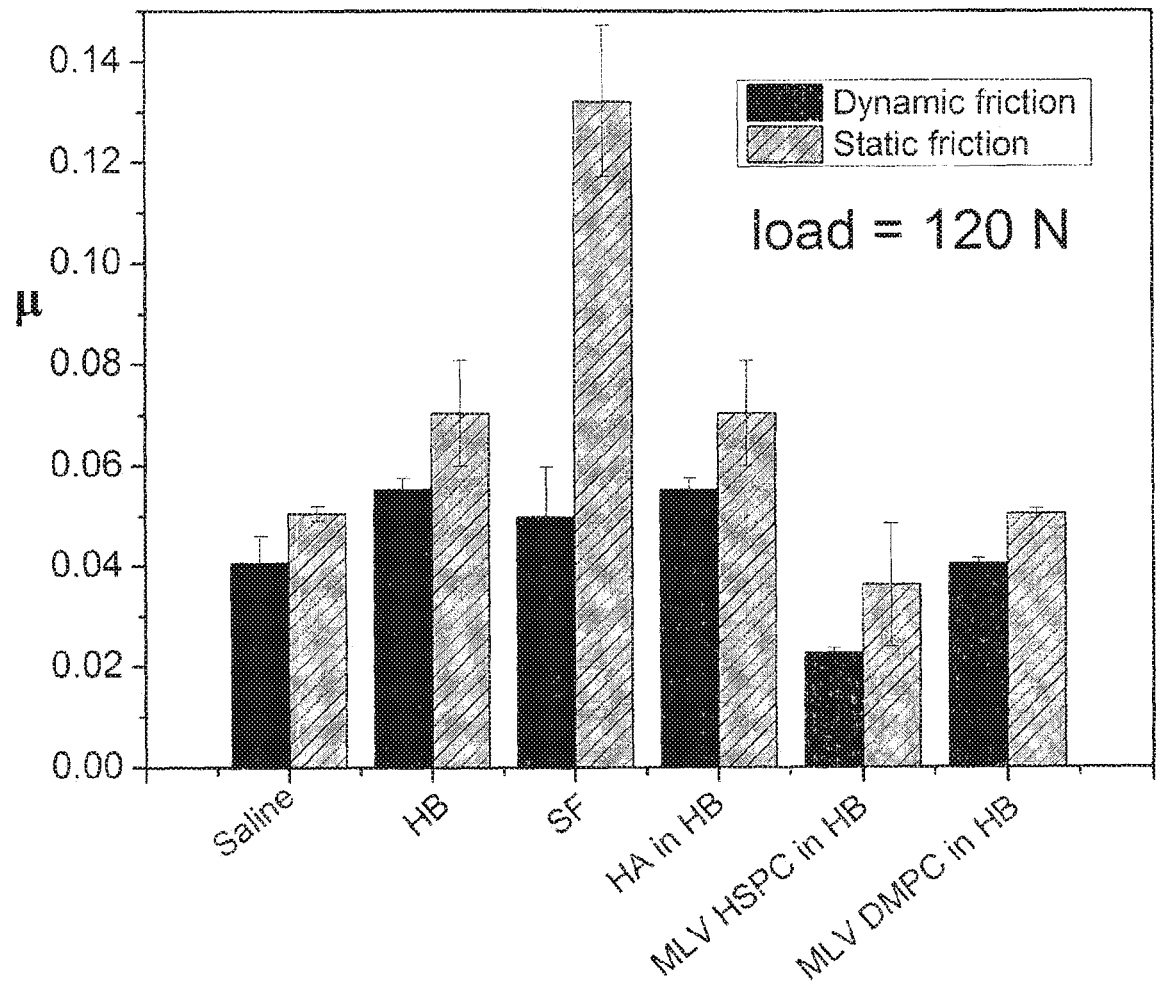

The invention claimed is:

1. A method for lubricating one or more non-biological surfaces of a replacement joint, comprising applying gel-phase liposomes onto said one or more surfaces, wherein the temperature of said surface(s) at the time of lubrication is below the liquid-crystalline to gel-phase transition temperature $T_m$ of said liposomes, wherein the gel-phase liposomes comprise two or more phosphatidylcholine lipids selected from the group consisting of hydrogenated soy phosphatidylcholine (HSPC), 1,2-distearoyl-sn-glycero-3-phosphocholine (DSPC) and dipalmitoylphosphatidylcholine (DPPC), wherein the molar ratio of the two or more phosphatidylcholine lipids being adjusted to produce liposomes having a $T_m$ value of not less than 45° C. and wherein the pressure applied to the surface is above 3 MPa.

2. The method according to claim 1, wherein the gel-phase liposomes have external polar head groups which are composed of at least 95 mole % phosphocholine groups, and of up to 5 mole % external non-phosphocholine head groups having an unperturbed-end-to-end radius in aqueous medium equal to or smaller than about 1 nm.

3. The method according to claim 2, wherein the gel-phase liposomes comprise a first lipid, which is phosphocholine-containing lipid selected from the group consisting of HSPC, DSPC, dipalmitoylphosphatidylcholine (DPPC) and mixtures thereof, and a second lipid, which carries trimethylammonium-propane (TAP) hydrophilic head group.

4. The method according to claim 3, wherein the TAP-containing lipid is selected from the group consisting of 1,2 ditetradecanoyl-3-trimethylammonium-propane (DMTAP), 1,2 dipalmitoyl-3-dimethylammonium-propane and 1,2-disteraroyl-3 dimethylammonium-propane.

5. The method according to claim 1, wherein the gel-phase liposomes are in the form of small unilamellar vesicles (SUV) and have a mean diameter which is smaller than 100 nm.

6. The method according to claim 1, wherein the gel-like liposomes are in the form of multilamellar vesicles (MLVs) and have a mean diameter which is larger than 200 nm.

7. The method according to claim 1, wherein the liposomes are applied in an aqueous medium which is an aqueous salt solution.

8. The method according to claim 1, wherein the surface to be lubricated is negatively-charged.

9. The method according to claim 1, wherein the pressure applied to the surface is greater than 6 MPa.

\* \* \* \* \*